United States Patent [19]

Clarke

[11] 4,447,235
[45] May 8, 1984

[54] THORACENTESIS DEVICE

[75] Inventor: John M. Clarke, 861 Sixth Ave. South, St. Petersburg, Fla. 33701

[73] Assignee: John M. Clarke, St. Petersburg, Fla.

[21] Appl. No.: 261,570

[22] Filed: May 7, 1981

[51] Int. Cl.³ .............................................. A61B 1/26
[52] U.S. Cl. .................................... 604/169; 128/760; 128/765
[58] Field of Search ................... 128/760, 763, 765, 4, 128/767, 768, 214.4, 764, 766, 347, 348; 604/169

[56] References Cited

U.S. PATENT DOCUMENTS

| | | | |
|---|---|---|---|
| 3,313,299 | 4/1967 | Spademan | 128/347 |
| 3,459,183 | 8/1969 | Ring et al. | 128/767 |
| 3,459,188 | 8/1969 | Roberts | 128/347 |
| 3,703,899 | 11/1972 | Calinog | 128/347 |
| 3,765,420 | 10/1973 | Felczak | 128/347 |
| 3,830,225 | 8/1974 | Shinnick | 128/4 X |
| 3,834,372 | 9/1974 | Turney | 128/748 |
| 3,952,729 | 4/1976 | Libman et al. | 128/765 |
| 4,099,528 | 7/1978 | Sorenson et al. | 128/348 X |
| 4,177,814 | 12/1979 | Knepshield et al. | 128/348 |
| 4,308,875 | 1/1982 | Young | 128/760 |

FOREIGN PATENT DOCUMENTS 575559  4/1924  France ............................ 128/214.4

Primary Examiner—George F. Lesmes
Assistant Examiner—Nancy A. B. Swisher
Attorney, Agent, or Firm—Joseph R. Slotnik

[57] ABSTRACT

A thoracentesis device which includes an elongated flexible catheter fixed at its proximate end to an elongated conduit which is aligned therewith. The conduit is provided with a seal which seals around a hollow needle which penetrates the seal means and passes through the conduit and the catheter and slightly beyond the catheter distal end. A vacuum source is connected to the proximate needle end. The seal also reseals the elongated conduit when the needle is removed. The conduit includes a valve which can be manipulated to connect the catheter to a side conduit when the needle is removed.

11 Claims, 12 Drawing Figures

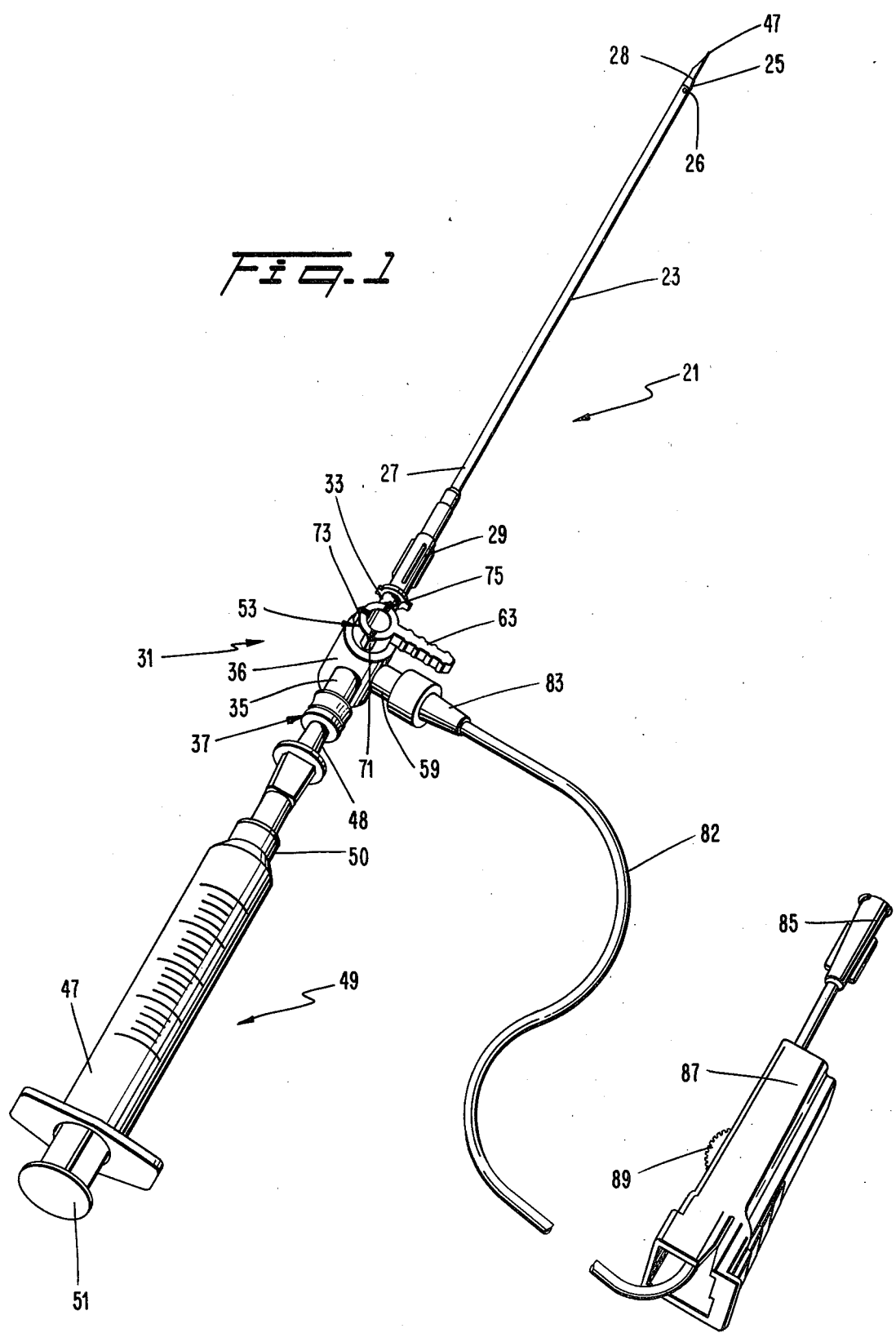

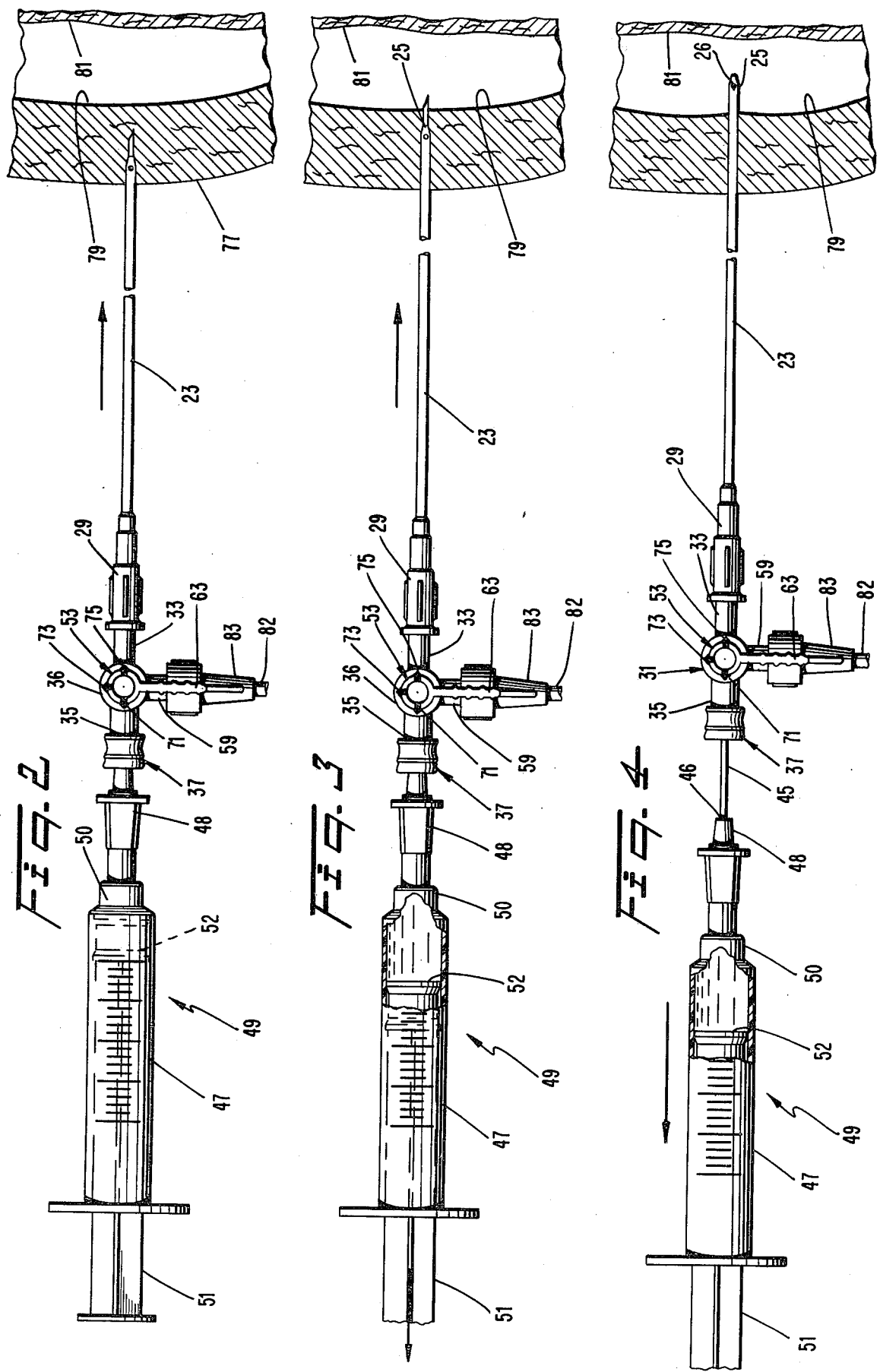

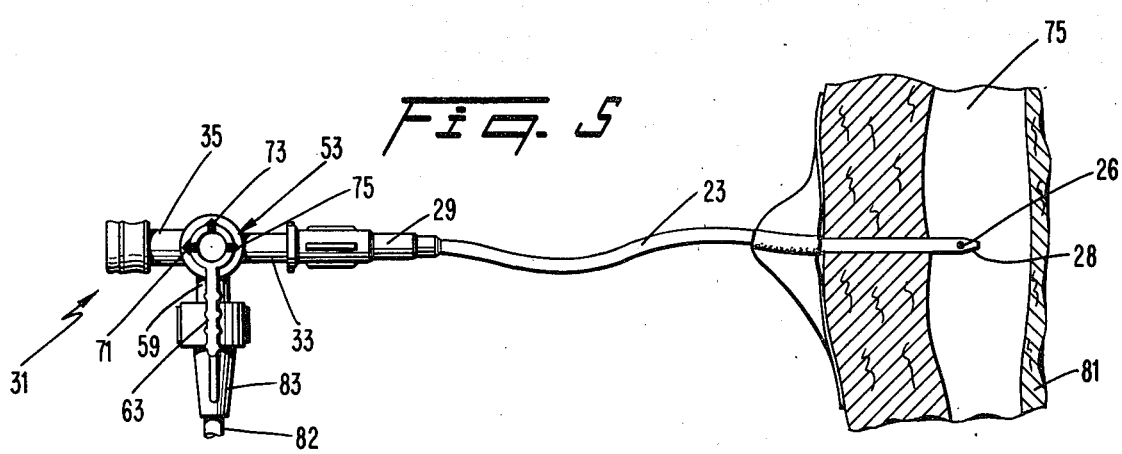
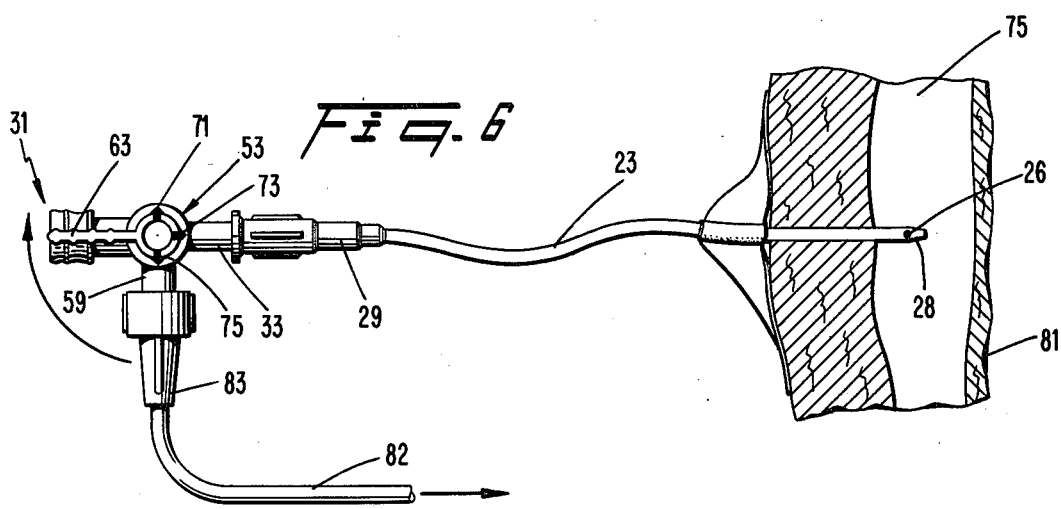
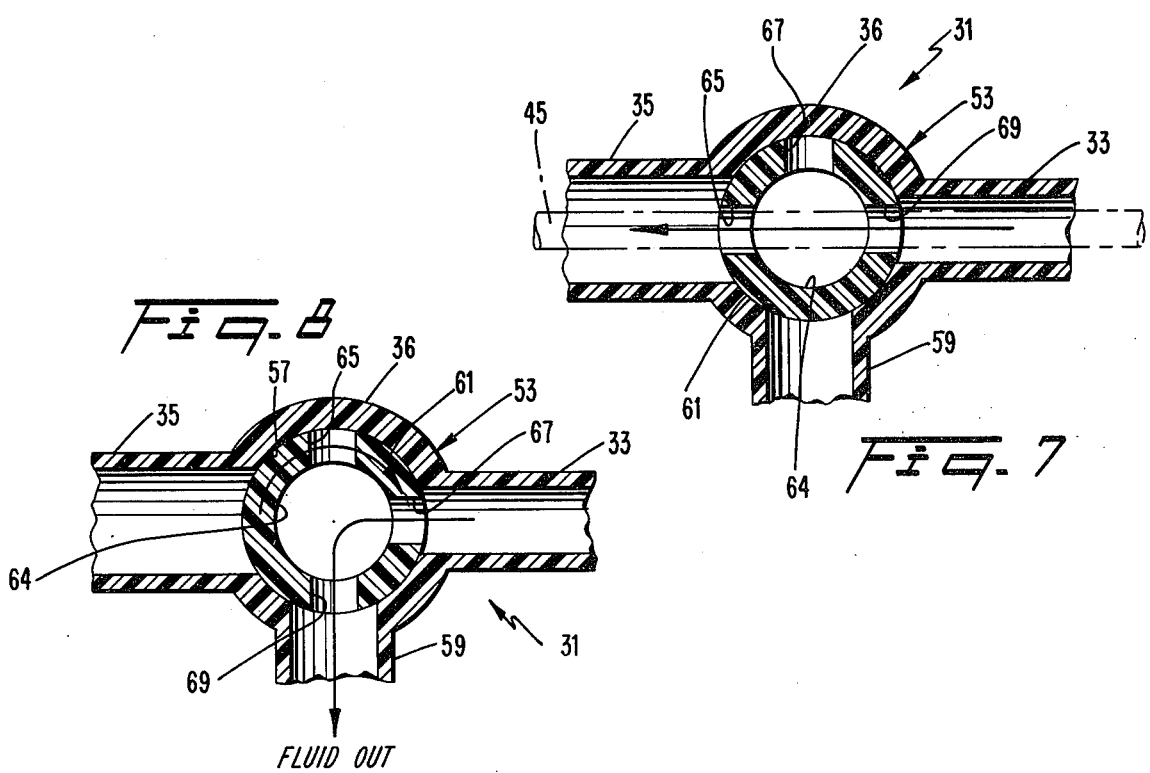

THORACENTESIS DEVICE

BACKGROUND OF THE INVENTION

The present invention relates to a thoracentesis device which is used in the removal of fluid from the pleural cavity, and more particularly to a thoracentesis device of this type which prevents air entry into the pleural cavity and lung puncture during its use.

In performing thoracentesis, an incision is made through the chest wall and a tube or catheter inserted through the incision into the pleural cavity. The proximate end of the catheter is connected to a negative pressure source e.g., a pump, and intrathorasic fluid, blood, air, or other secretions are then removed from the pleural cavity through the catheter.

Removal of fluid or other materials from the pleural cavity presents problems which are unique to this body cavity. In order for the lungs to remain expanded, there must be a negative pressure within the pleural cavity. Any communication between the pleural cavity and atmospheric pressure can result in a sudden rush of air from outside the body into the pleural cavity. This can produce a collapsed lung and a medical condition known as pneumothorax. Thus, it is important to insure that the pleural cavity is at all times sealed from atmospheric air.

A common method of making the chest wall incision in this procedure is to use a needle. However, if a needle is introduced into the pleural cavity too far, it can puncture the surface of the lung. In this case, air from the lung air spaces (alveoli) or from the air passages (bronchi) can escape into the pleural cavity and can produce a lung collapse (pneumothorax). This is a dangerous condition because air can continue to escape from the lung and produce a pressure within the pleural cavity which is actually greater than atmospheric pressure. This condition is known as tension pneumothorax and can produce serious interference with cardiac function and possible death.

SUMMARY OF THE INVENTION

The present invention overcomes the problems discussed above by providing a thoracentesis device which is operable to prevent communication between the pleural cavity and the atmosphere, and to prevent puncture of the lung.

Another object of this invention is to provide a thoracentesis device of the above character which is relatively easy to use.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

To achieve the objects in an accordance with the purpose of the invention, as embodied herein, the thoracentesis device of this invention comprises an elongated flexible catheter having a distal end and a proximate end, means defining an elongated conduit connected to the proximate end of the catheter and in line therewith, seal means in the elongated conduit means and operable to seal the conduit means, a hollow needle having a sharpened distal end adapted to penetrate the seal means and to extend through the conduit means and the catheter and beyond the distal end thereof, means for applying negative pressure to the needle, the seal means being self-sealing and operable to re-seal the conduit means upon complete withdrawal of the needle from the conduit means, and valve means in the conduit means between the seal means and the catheter operable in a first position to connect the catheter to a side conduit means extending laterally of the elongated conduit means, and in a second position to block communication between elongated conduit means and the side conduit means.

The accompanying drawings which are incorporated in and constitute a part of this specification, illustrate one embodiment of the invention and, together with the description, serve to explain the principles of the invention.

BRIEF DESCRIPTION OF THE DRAWINGS

FIG. 1 is a perspective view of a thoracentesis device constructed in accordance with the present invention;

FIG. 2 is a plan view illustrating use of the device of this invention with the needle point and distal catheter end penetrating a chest wall;

FIG. 3 is a view similar to FIG. 2 showing the needle point having penetrated the chest wall and fluid being withdrawn from the pleural cavity into a syringe;

FIG. 4 is a view similar to FIG. 3 and showing the needle being withdrawn from the catheter and the distal catheter end in the pleural cavity;

FIG. 5 is a view similar to FIG. 4 showing the needle completely withdrawn from the device;

FIG. 6 is a view similar to FIG. 5 showing the parts in position for removal of intrathorasic fluid from the pleural cavity;

FIG. 7 is an enlarged sectional view showing a valve utilized in the device of the present invention with the parts in position as shown in FIGS. 2-5;

FIG. 8 is a view similar to FIG. 7 and showing the parts in the position of FIG. 6 for intrathorasic fluid removal;

DESCRIPTION OF THE PREFERRED EMBODIMENT

Figure 9:
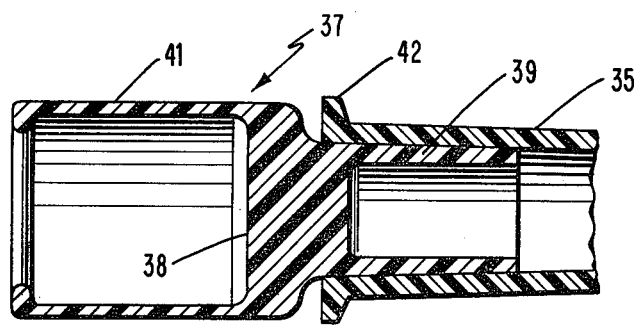
FIG. 9 is an enlarged sectional view illustrating a seal means utilized in the present invention prior to complete assembly thereof.

Reference will now be made in detail to the present preferred embodiment of the invention, an example of which is illustrated in the accompanying drawings.

The preferred embodiment of thoracentesis device is shown in FIG. 1 and is represented generally by the numeral 21. As embodied herein, this device includes an elongated flexible catheter 23 having a distal end 25 formed with one or more radial ports or openings 26. The catheter 23 has a proximate end 27 connected to an elongated conduit means 31 which is in line with the catheter 23. The catheter distal end 25 may be tapered as shown at 28 for a purpose to be described (see also FIGS. 5, 6 and 12). The elongated conduit means 31 includes a pair of hollow, aligned arms 33, 35 joined by a hollow, intermediate barrel 36 (see also FIGS. 7 and 8). An adaptor 29 is fixed to the proximate end 27 of the catheter 23 and fits snugly on the arm 33.

Figure 10:
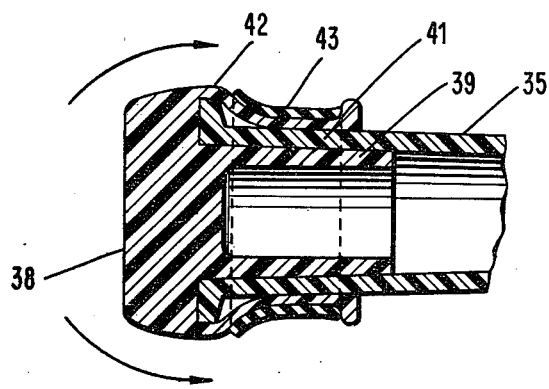
FIG. 10 is a view similar to FIG. 9 and showing the seal means after complete assembly.
Figure 11:
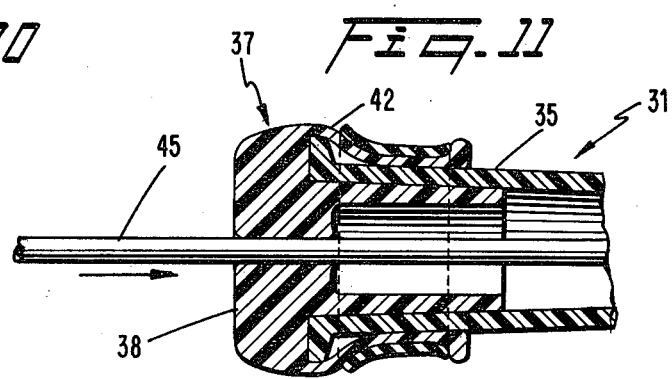
FIG. 11 is a view similar to FIG. 10 and showing the needle of the present invention penetrated through the seal means.

In accordance with the invention, seal means is provided in the elongated conduit means which is operable to seal the elongated conduit means. As embodied herein, an elastomeric seal 37 includes a thickened body of material 38 formed with an elongated plug 39 which sealingly fits into the end of arm 35 of elongated conduit means 31 (see FIG. 9). The seal 37 also includes a stretchable sleeve 41 which is adapted to be folded back over the body 38 and plug 39. This allows the sleeve 41 to be folded over an annular flange 42 on the end of arm 35 after the plug is inserted into the arm (see FIG. 10). A heat sensitive shrink tubing 43 can then be placed over the sleeve portion 41 to hold it in place on the arm 35 (see FIG. 11).

In accordance with the present invention, a hollow needle having a sharpened distal end is adapted to penetrate the seal means and to extend through the elongated conduit means and catheter and beyond the distal end of the catheter. As embodied herein, a hollow needle 45 has a sharpened distal end 47 which can penetrate through the seal means 37 which is in place on the arm 35 so that the needle 45 can pass completely through the seal (see FIG. 11). The needle 45 is sized to pass freely through the aligned hollow arms 33, 35 of the conduit means 31 and all the way through the catheter 23 so that the sharpened distal end 47 of the needle extends a short distance beyond the distal end 25 of the catheter 23 (see FIG. 1). The needle 45 has a proximate end 46 which is fixed to a connector 48 which is engageable with the seal means 37 to limit axial movement of the needle 45 relative to the seal means 37. The nature of the elastomeric material of the seal 37 is such that the sharpened end 47 of the needle 45 parts and stretches the material of the seal body 38 as it passes therethrough so that an effective and reliable seal is formed around the needle 45.

In accordance with the invention, means is provided for applying negative pressure to the needle. As embodied herein, the connector 48 joins the proximate end 46 of the needle 45 to a hollow projection 50 on the end of a tube 47 forming part of a syringe 49 (see FIG. 4). A plunger 51 is slidable within the tube 47 and is provided with a grommet 52 which slidably engages the inner surface of the tube 47 so that when the plunger 51 is withdrawn outwardly of the tube 47 (or toward the left as seen in FIGS. 3 and 4), a negative pressure is applied to the needle 45.

In accordance with the invention, the seal means is self-sealing and is operable to re-seal the elongated conduit means upon withdrawal of the needle from the elongated conduit means. As embodied herein, the needle 45 can be withdrawn from the catheter 23 and conduit means 31 simply by pulling back on the syringe 49 and connector 48. When the needle 45 is withdrawn from the seal means 37, the elastomeric material of the seal body contracts and closes the opening which was formed by the needle 45 so that the conduit means 31 is re-sealed.

In accordance with the invention, valve means is provided in the elongated conduit means between the seal means and the catheter and is operable in a first position to connect the catheter to a side arm extending laterally of the aligned arms of the elongated conduit means. In a second position, the valve means is operable to communicate the aligned arms and to block communication between the aligned arms and the side arm. As embodied herein, a valve 53 is positioned between arms 33, 35 of the elongated conduit means 31. The illustrated valve 53 is a stopcock type which includes hollow barrel 36 which defines an internal cylindrical bore 57 in communication with aligned arms 33, 35 (see FIGS. 7 and 8). The valve bore 57 is also in communication with a hollow side arm 59 which extends laterally of and is between aligned arms 33, 35.

As further embodied herein ad shown in FIGS. 7 and 8, the valve 53 includes a hollow cylindrical stopcock 61 which is rotatably fitted in the bore 57. The stopcock 61 extends through one end of the barrel 36 and has an external lever 63 fixed thereto (see FIGS. 1-6). The stopcock 61 is provided with a central bore 64 and with three radial ports 65, 67, 69, ports 65 and 69 being aligned and disposed 90° to either side of port 67. In a first position of the stopcock 61, shown in FIG. 8, arm 33 and side arm 59 are communicated by ports 67, 69 and bore 64 while communication to the arm 35 is blocked. In a second position, shown in FIG. 7, ports 69 and 65 which are aligned with each other are also aligned and communicated with arms 33, 35, respectively. In this position, arms 33, 35 are in communication with one another through ports 65, 69 and bore 64 while communication to the side arm 59 is blocked. The external end of stopcock 61 may be provided with indicia, here, arrows 71, 73, 75 which are aligned with ports 65, 67, 69 respectively, to indicate the position of these ports.

In use, the valve stopcock 61 is positioned as shown in FIG. 7 and in FIGS. 1-6 and the needle 45 is passed through the seal 37, through the conduit means 31 including the aligned arms 31, 33 and aligned ports 65, 69, and the catheter 23 to the extent where connector 48 abuts seal means 37, as shown in FIG. 1. In this position, the sharpened distal point 47 extends slightly beyond the distal end 25 of the catheter 23. The needle 45 fits closely within the catheter 23 and rigidly supports it. The aligned ports 65, 69 in the valve stopcock 61 allow the needle to pass through the valve 53 while communication to the side arm 59 is blocked.

The device 21 is now ready for use in thoracentesis. As shown in FIG. 2, the sharpened needle point 47 is used to penetrate a chest wall 77 toward a pleural cavity 79 of a patient. The tapered end 28 of catheter 23 follows closely behind the needle point 47 through the chest wall and, as soon as the distal catheter end 25 is into the chest wall a negative pressure is applied to the needle 45 by the syringe 49 by pulling rearwardly on the plunger 51 (see FIG. 2).

Penetration of the needle point 47 and catheter 23 is resumed and when the needle point 47 passes through the chest wall 77 and into the pleural cavity 79 (FIG. 3), the negative pressure on the needle 45 causes fluid in the pleural cavity 79 to be drawn through the needle 45 into the syringe 49. This will be visible immediately to the surgeon so that he knows the needle point 47 has reached the pleural cavity 79. The device is inserted slightly further to insure that the catheter distal end 25 and openings 26 are in the pleural cavity 79 but not far enough for the needle point 47 to penetrate the lung 81.

The needle 45 is now withdrawn completely from the catheter 23 and the conduit means 31 and the catheter 23 held in place by hand during the thoracentesis procedure. Once the needle 45 is withdrawn, danger of lung puncture is substantially eliminated even if the distal catheter end 25 engages the lung 81 since the catheter 23 is flexible and its distal end 25 relatively blunt. Further, when the needle 45 is withdrawn from the seal means 37, the material of the seal means contracts and re-seals the opening which was formed by the needle 45. This blocks fluid flow through the elongated conduit means 31 and prevents air from entering the elongated conduit means 31 and the catheter 23.

To remove completely the fluid or other matter from the pleural cavity 79, the stopcock 61 now is turned to the position shown in FIG. 6 after the needle 45 is withdrawn so that arm 33 and catheter 23 are now in communication with side arm 59 (see FIG. 8). A tube 82 is connected at one end to the side arm 59 by an adaptor 83 and its other end is provided with an adapter 85 (FIG. 1) which is used to connect the tube 82 to a vacuum source such as a vacuum bottle or the like. Thus, the vacuum bottle (not shown) is used to withdraw the fluid or other matter from the pleural cavity 79. Desirably, a regulator 87 (FIG. 1) is positioned on the tube 81 to control the rate at which fluid is withdrawn from the pleural cavity 79. The regulator 87 is provided with a thumb manipulable cam wheel 89 which is movable from a position where the tube 81 is fully open to a position where the tube 81 is clamped shut.

It will be appreciated that the entire process described above is carried out without allowing communication between the atmosphere and the pleural cavity 79 which would allow air to enter and cause lung collapse. Thus, the proximate end of the needle 45 and catheter 23 are sealed from the atmosphere by the seal means 37 and by the syringe 49. In fact, a negative pressure is applied to the needle 45 by the syringe 49 as the needle and catheter enter the pleural cavity. When the needle 45 is withdrawn, the catheter 23 remains sealed from the atmosphere by the self-sealing seal means 37. When the valve 53 is then positioned to communicate the catheter 23 and the tube 81 and the vacuum pump (not shown) is turned on, fluid is removed from the pleural cavity. The regulator 87 is adjusted by moving cam wheel 89 to control the rate of fluid removal.

Figure 12:
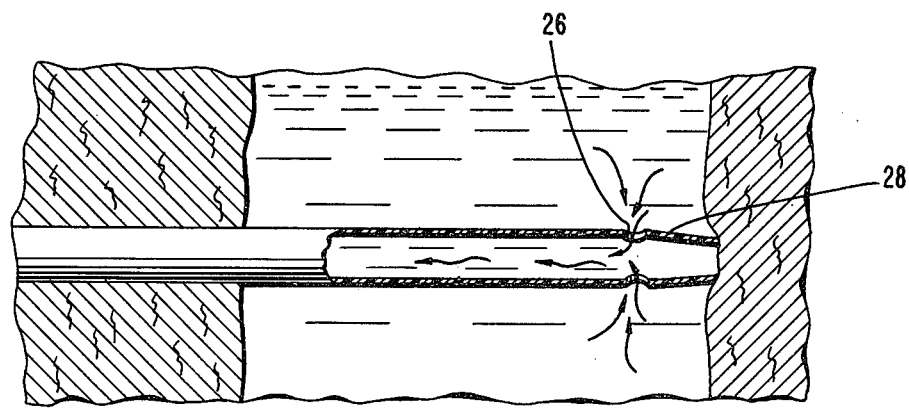
FIG. 12 is an enlarged view partly in section showing the distal catheter end in position in the pleural cavity with fluid from the pleural cavity being withdrawn through the catheter.

It will be appreciated that the catheter 23 is a relatively flexible tube. The needle 45 supports the catheter 23 during insertion into the pleural cavity 79 but since the needle 45 is withdrawn after penetration into the pleural cavity, the danger of puncturing the lung 80 by the needle point 47 is substantially eliminated. Once the needle 45 is withdrawn from the catheter 23, the catheter 23 is sufficiently flexible so as not to pose a threat regarding lung puncture. In fact, the catheter 23 can engage the wall of the lung 81 as shown in FIG. 12. In the event that happens, the openings 26 in the catheter 23 adjacent its distal end 25 allow for withdrawal of fluid from the pleural cavity 75.

It will be apparent to those skilled in the art that various additions, substitutions, modifications, and omissions can be made to the thoracentesis device of the present invention without departing from the scope or spirit of the invention. Thus, it is intended that the present invention cover the additions, substitutions, modifications, and omissions provided they come within the scope of the appended claims and their equivalents.

What is claimed is:

1. A thoracentesis device comprising an elongated flexible catheter having a distal end and a proximate end, means defining an elongated conduit including a value means and connected to the proximate end of said catheter and in line therewith, seal means at the distal end of said elongated conduit means continuously sealing said conduit means and the proximate end of said catheter from the atmosphere, a hollow needle having a sharpened distal end adapted to penetrate said seal means and to extend through said conduit means and said catheter and beyond the distal end thereof, means connected to the proximate end of said hollow needle for applying negative pressure to said needle, said needle being operable for complete withdrawl from said elongated conduit means and said seal means, said seal means being self-sealing and re-sealing said conduit means upon complete withdrawal of said needle from said conduit means and separation of said needle from said conduit means, said valve means being between said seal means and said catheter and said valve means movable to a first position where it connects said catheter to a side conduit means connected to and extending laterally of said elongated conduit means, and to a second position where it blocks communication between said elongated conduit means and said side conduit means.

2. A thoracentesis device as claimed in claim 1, said negative pressure applying means including a syringe connected to the proximate end of said needle.

3. A thoracentesis device as claimed in claim 1, including a vacuum source connected to said side conduit means for removal of fluid from the pleural cavity when the catheter distal end is in the pleural cavity, the needle withdrawn, and the valve means in the first position.

4. A thoracentesis device as claimed in claim 1, said elongated conduit means comprising a pair of hollow aligned arms joined by a hollow, intermediate barrel, said valve means comprising a stopcock rotatable in said intermediate barrel and formed with a pair of aligned radial ports which are aligned with said aligned arms in said second valve means position, whereby said needle can pass through said aligned arms and said aligned ports.

5. A thoracentesis device as claimed in claim 4, said side conduit means comprising a hollow arm connected to said hollow barrel and extends laterally of and is between said aligned arms, said stopcock having a third radial port which is between and disposed 90° with respect to said pair of radial ports.

6. A thoracentesis device as claimed in claim 5, said stopcock ports communicating only the side conduit lateral arm with the aligned arm between said intermediate barrel and said catheter in said first valve position, said stopcock ports communicating only said aligned arms in said second valve position.

7. A thoracentesis device as claimed in claim 5, said stopcock having a lever fixed thereto and disposed externally of said intermediate barrel for manipulation of said stopcock, said lever including indicia means indicating the positions of said stopcock ports.

8. A thoracentesis device as claimed in claim 4, said seal means including an elastomeric member in one of said hollow arms between said intermediate barrel and said negative pressure applying means, said elastomeric member being adapted to seal around said hollow needle when penetrated therethrough.

9. A thoracentesis device as claimed in claim 6, said seal means including a thickened body of material formed with an elongated plug which sealingly fits into said one of said hollow arms, said seal further including a stretchable sleeve which is adapted to be folded back over the thickened body and said one hollow arm after the plug is inserted into said arm.

10. A thoracentesis device as claimed in claim 9, said seal further including a heat sensitive shrink tubing which is placed over the sleeve portion to hold it in place on said one arm.

11. A thoracentesis device as claimed in claim 1, said catheter having side ports therein adjacent to its distal end.

* * * * *

UNITED STATES PATENT AND TRADEMARK OFFICE
CERTIFICATE OF CORRECTION

PATENT NO. : 4,447,235

DATED : May 8, 1984

INVENTOR(S) : JOHN M. CLARKE

It is certified that error appears in the above-identified patent and that said Letters Patent is hereby corrected as shown below:

Column 5, line 67, change "value" to -- valve --;

Column 5, line 68, change "distal" to -- proximate --.

Signed and Sealed this

Eighteenth Day of September 1984

[SEAL]

Attest:

GERALD J. MOSSINGHOFF

Attesting Officer    Commissioner of Patents and Trademarks